United States Patent [19]
Tauber et al.

[11] Patent Number: 5,980,712
[45] Date of Patent: Nov. 9, 1999

[54] SINGLE-ROD MEASURING ELEMENT FOR ELECTROCHEMICAL MEASUREMENTS

[75] Inventors: Günter Tauber, Kriftel; Axel Lauck, Ober-Hilbersheim; Peter Henrich, Kriftel., all of Germany

[73] Assignee: Schott Gerate GmbH, Hofheim/Ts., Germany

[21] Appl. No.: 09/048,158

[22] Filed: Mar. 26, 1998

[30] Foreign Application Priority Data

Mar. 26, 1997 [DE] Germany .............. 297 05 433

[51] Int. Cl.[6] .................................................. G01N 27/26
[52] U.S. Cl. .................. 204/435; 204/400; 204/416; 204/420; 204/279
[58] Field of Search .................. 204/279, 420, 204/416, 435, 400; 435/307.1; 220/812

[56] References Cited

U.S. PATENT DOCUMENTS

| | | |
|---|---|---|
| 3,530,056 | 9/1970 | Haddad ............................... 204/420 |
| 3,582,474 | 6/1971 | Hair et al. .......................... 204/420 |
| 4,401,548 | 8/1983 | Brezinski ........................... 204/420 |
| 4,608,148 | 8/1986 | Frollini, Jr. et al. ................ 204/420 |
| 4,620,918 | 11/1986 | Bukamier et al. ................... 204/403 |
| 4,770,762 | 9/1988 | Schrimm et al. ................... 204/279 |
| 5,397,452 | 3/1995 | Buck et al. ........................ 204/420 |
| 5,567,291 | 10/1996 | Melzer .............................. 204/420 |
| 5,830,338 | 11/1998 | Seto et al. ......................... 204/416 |

*Primary Examiner*—Robert Warden
*Assistant Examiner*—Kaj K. Olsen
*Attorney, Agent, or Firm*—Millen, White, Zelano & Branigan

[57] ABSTRACT

A single rod measuring probe has a hollow probe portion which contains an electrolyte solution and an electrical connector plug. The hollow probe portion and electrical connector plug are joined by a refill unit which receives the probe portion and plug in opposite ends thereof. The refill unit includes a lateral opening for filling the probe portion with electrolyte solution and a slidable cover for closing the opening. The slidable cover includes an elastic seal which seals the lateral opening when the cover is over the lateral opening. Preferably, the refill unit is non-circular in cross-section to facilitate venting.

12 Claims, 2 Drawing Sheets

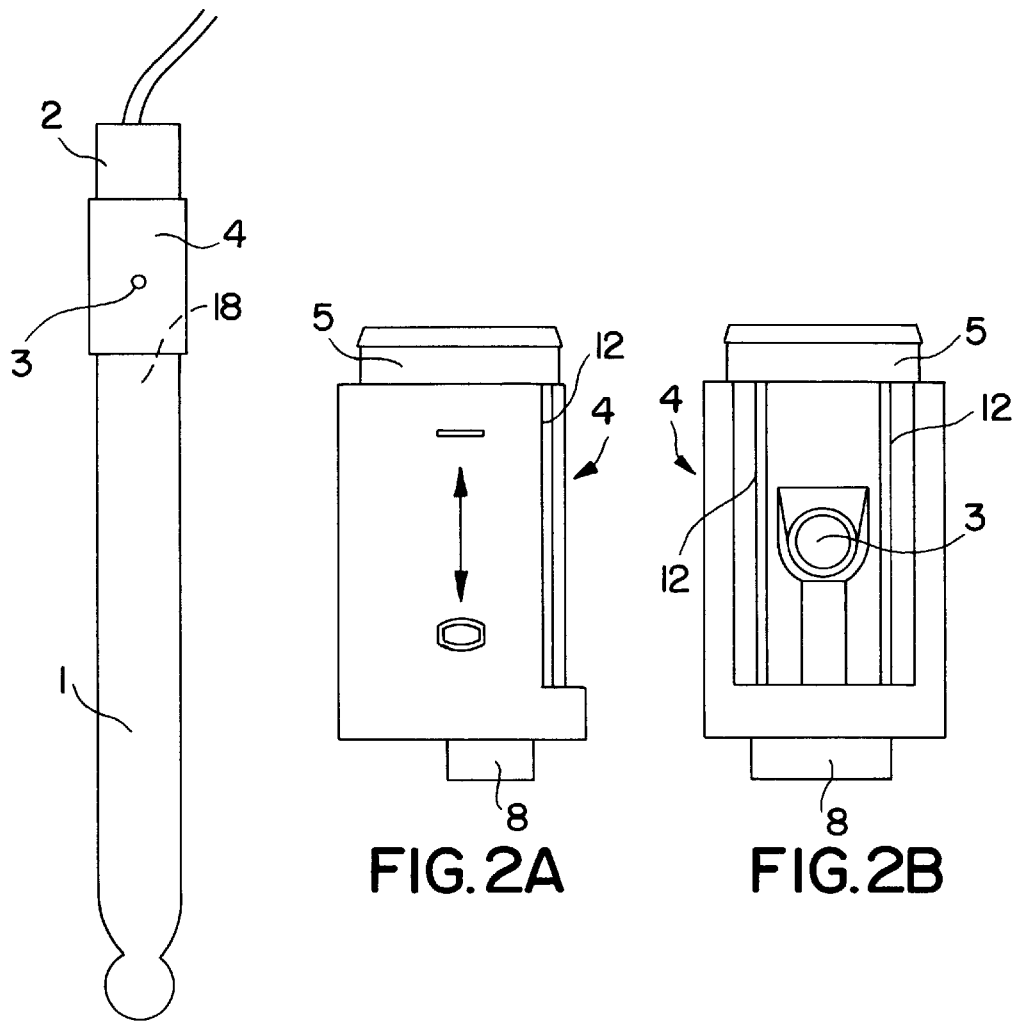
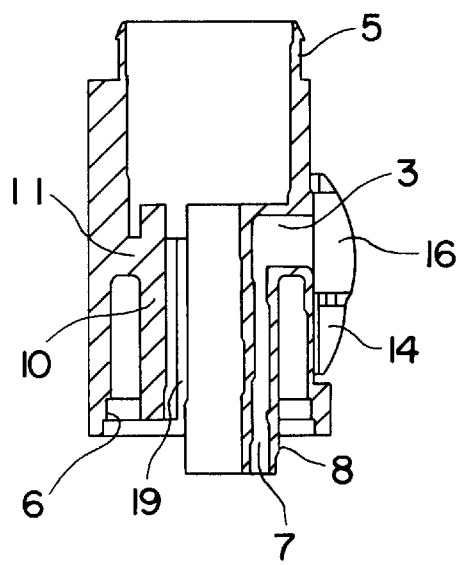

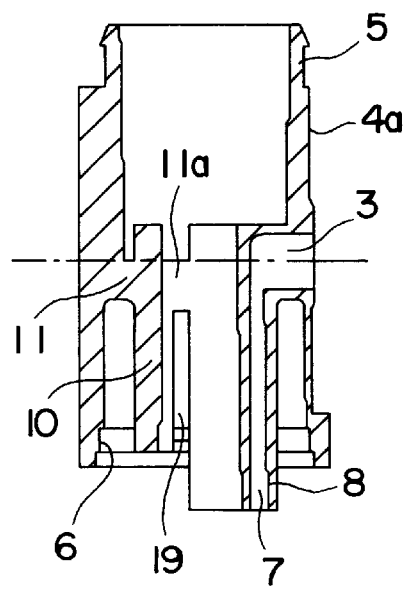
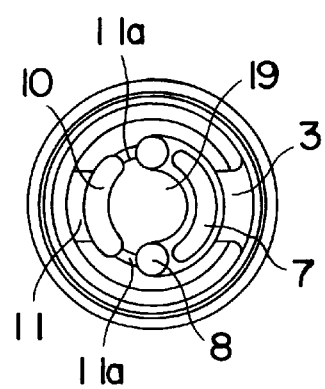
FIG.4A    FIG.4B
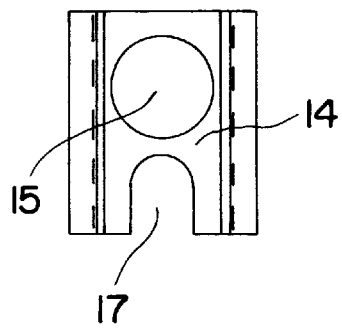
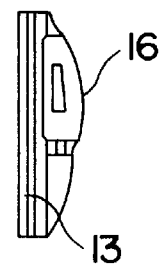
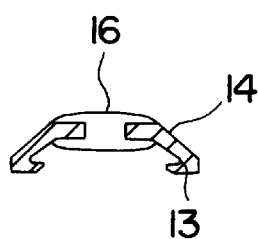
FIG.5A    FIG.5B    FIG.5C

SINGLE-ROD MEASURING ELEMENT FOR ELECTROCHEMICAL MEASUREMENTS

FIELD OF THE INVENTION

The invention relates to a single-rod measuring probe for electrochemical measurements, with a cylindrical housing which is made of glass or plastic. More particularly, the invention relates to such a probe which is filled with an electrolyte solution, and in which an electrode is installed as a sensor.

BACKGROUND OF THE INVENTION

Single-rod measuring probes for electrochemical measurements are components of electrochemical measuring elements used in the field of sensor analysis. They are especially useful for determining pH and redox voltage. These measuring probes in most cases contain a reference electrode, which is installed in a cylindrical housing that is made of glass or plastic. In reference electrodes, an electrolyte solution, in most cases a KCL solution, has to be refilled intermittently with liquid electrolyte. When this is the case, the design of the refill opening causes problems.

Single-rod measuring probes are known which in the top of the electrodes have an axial hole with a circular cross-section for use as a refill channel, which channel can be sealed with a plug.

In the vast majority of the known single-rod measuring elements, the refill opening is made in the housing wall, i.e. in the electrolyte chamber wall, either directly as a hole or with an upstream radially-projecting nozzle or a laterally-projecting elevated refill olive, whereby both the opening and the nozzle or the olive have circular cross-sections and can be sealed with a plug or tube section.

The refill openings in the known single-rod measuring chains primarily have the drawback of awkward handling and/or inadequate tightness.

In several types, handling is made more difficult by accessories for filling the electrode housing; however, such accessories are not always available. In other types, sealing devices are provided that are difficult to handle or are inadequate.

A more general drawback of the known measuring elements with refill openings having circular cross-sections is that during refilling, electrolyte is spilled since the air in the electrolyte space cannot escape (bubble-free).

SUMMARY OF THE INVENTION

An object of the invention is to improve refilling, as well as to avoid spilling electrolyte solution in single rod measuring elements used for electrochemical measurements.

The achievement of this object according to the invention is accomplished by mounting between the housing and the electric connecting unit a separate refill unit which has a refill opening. The refill unit is made of plastic and has a refill channel that provides access to the inside of the housing with the refill opening, the unit having a cross-section that is non-circular.

Better handling ability is achieved in that the refill opening is no longer made, as in the prior art, by an opening in the glass or plastic shaft of the electrolyte chamber, but rather in the refill unit which can be mounted separately between the sensor and the electric connecting unit.

Because the refill channel is made, at least in significant portions of its area, with a cross-section that deviates from a circle, ventilating the electrolyte space is advantageously made possible during filling, so that the electrolyte solution can be filled without bubbles and, consequently, is not spilled.

An especially advantageous ventilation follows when, according to a further development of the invention, the cross-section of the refill channel is circular and preferably is made by a segment of a circle.

According to a preferred embodiment of the invention, the drawbacks of the known sealing devices that are difficult to handle or are inadequately effective are avoided. This is because, in this invention, guides that are undercut on the refill unit are provided for a slide which is made of plastic and which has a rubber-elastic seal for sealing the refill opening at a specific slide position.

The plastic slide with a rubber seal makes the refill opening advantageously easy to handle and seals it effectively. The advantage of easy handling is ensured in this case by the narrow-tolerance design features of the plastic parts, which can be produced in the injection-molding process, as is generally known, with very tight tolerances.

Other design features, as well as advantages of the invention, are presented below in the description of an embodiment, which is depicted in the drawings.

BRIEF DESCRIPTION OF THE DRAWINGS

Various other features and attendant advantages of the present invention will be more fully appreciated as the same becomes better understood when considered in conjunction with the accompanying drawings, in which like reference characters designate the same or similar parts throughout the several views, and wherein:

FIG. 1 is a side view of a single-rod measuring chain with a refill unit according to the invention that can be mounted separately between the electrolyte housing and electric connecting unit;

FIG. 2A is an enlarged side view of the refill unit of the invention according to FIG. 1;

FIG. 2B is an enlarged front view of the refill unit of FIG. 2A;

FIG. 3 is a longitudinal section through the refill unit of the invention according to FIG. 2A with a sealing slide mounted there;

FIG. 4A is a longitudinal section through the refill unit of the invention according to FIG. 2, FIG. 4B is a cross-section B, made along line of intersection B—B in FIG. 4A;

FIG. 5A is a top view of the sealing slide of the refill unit;

FIG. 5B is a longitudinal cross section through the sealing slide of FIG. 5A; and FIG. 5C is a lateral cross-section through the refill unit of FIG. 5A.

DETAILED DESCRIPTION

FIG. 1 shows a single-rod measuring probe for electrochemical measurements with a cylindrical housing or probe portion 1 which is made of glass or plastic, which is filled with an electrolyte solution, and in which an electrode is installed as a sensor in a known way, not shown. Between said housing 1 and a top-side electrical connecting unit 2, which is an electrode plug-in head, a separate refill unit 4 configured in accordance with the invention is mounted that has a refill opening 3 and is made of plastic.

The refill unit 4 according to FIGS. 2–5 is comprised of a hollow-cylindrical plastic part 4a, a connecting nozzle 5 for the electrode plug-in head 2, inner threading 6 (see FIG. 3) for connecting to the housing 1, and a refill channel 7 that is connected to the refill opening 3 and forms the access to the inside of the housing. The housing 1 is designed to receive an arcuate segment 8 defining the refill channel 7 as well as a solid arcuate segment 10, which segment 10 is molded to the latter inside the hollow cylinder, via a bridge 11, and which forms a cylindrical guide together with opposing partial section 8 with refill channel 7, which is connected to the latter via bridge 11a.

As is evident from FIGS. 3 and 4, the housing or probe 1 is threaded into the refill unit 4 by inner threading 6 with the non-circular segment 8 having channel 7 projecting through the open mouth 18 of the housing or probe 1 but not plugging the open mouth. That the housing or probe 1 has an open mouth 18 is evident because this invention relates to a single-rod measuring probe having an axial hole with a circular cross section for use as a refill channel, which axial hole is an open mouth. Instead of sealing the channel with a plug as is set forth in the "Background of the Invention", the channel receives the non-circular segment 8 which allows venting via the axial opening 19 through the refill unit 4.

Dovetail-shaped guides 12 that are undercut according to FIG. 2 are made on refill unit 4 for receiving complementary guide means 13 of a plastic sealing slide 14 according to FIGS. 5A–C. Sealing slide 14 also has an opening 15, which is sealed with a rubber-elastic sealing element 16 when the sealing element is slid thereover, as well as an archway-like recess 17, which opens filling opening 3 in position I of the sealing slide (see labeling according to FIG. 2A). Conversely, the filling opening 3 is effectively closed according to FIG. 3 by sealing element 16 when slid to the O-position. Preferably, the sealing element 16 is in the form of an elastic rivet and is moved between a first position of the sealing slide 14 which seals the opening 3 and a second position of the sealing slide which uncovers the opening 3.

The entire disclosure of all applications, patents and publications, cited above and below, and of corresponding German application No. 297 05 433.3, filed Mar. 26, 1997 is hereby incorporated by reference.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A single-rod measuring element for electrochemical measurements comprising a probe in the form of a cylindrical housing (1) made of glass or plastic which is filled with an electrolyte solution and has an electrode installed therein as a sensor, the housing having a housing axial opening (18) for electrolyte solution and a topside electrical connecting unit (2); wherein between housing (1) and the electrical connecting unit (2) is mounted a separate refill unit (4) having a lateral refill opening (3) therein, the refill unit (4) having an axial refill channel (7) for accessing the inside of the housing (1) which the axial refill channel (7) is connected to the lateral refill opening (3) and has an arcuate cross-sectional shape that aligns with the housing opening (18) but does not close the housing refill opening (18)so that the housing (1) vents as electrolyte is introduced through the external lateral refill opening (3).

2. A single-rod measuring element according to claim 1, wherein the cross-sectional shape of the refill unit (4) is circular.

3. A single-rod measuring element according to claim 2, wherein guides (12) which are present on the refill unit and are undercut on the sides for mounting a slide (14) which is made of plastic and which is provided with a rubber-elastic seal (16) to seal the lateral refill opening in a specific slide position.

4. The single rod measuring element of claim 1 wherein the refill unit (4) is made of plastic and spaces the housing (1) from the electrical connecting unit (2) while connecting the housing and unit.

5. The single rod measuring element of claim 1 wherein the refill unit (4) has a vent (19) therethrough.

6. A refill unit adapted for use with a single rod measuring device having a probe portion and a plug-in head portion, the fill unit comprising:

a first end adapted to receive the probe portion and a second end adapted to receive the plug-in head portion;

a central opening extending axially therethrough from the first end to the second end;

a lateral opening into which electrolyte solution is introduced;

an axial channel connected to the lateral opening at one end and having an opening at the other end for directing the electrolyte solution to the probe;

a pair of rails straddling the lateral opening;

a sliding cover mounted on the rails for sliding movement from a first position which seals the lateral opening to a second position which uncovers the lateral opening; and a seal on the sliding cover to seal the lateral opening when the sliding cover is in the first position.

7. A refill unit according to claim 6, wherein the sides of the rails are under-cut in opposite directions and dovetail in grooves in the sliding cover.

8. A refill unit according to claim 7, wherein the seal is an elastic rivet on the slidable cover having a first surface which seals with the lateral opening and a second surface providing a gripping area which facilitates sliding the cover from the first position to the second position to uncover the lateral opening and from the second position to the first position to seal the lateral opening.

9. A refill unit according to claim 8, wherein the slidable cover includes a slot therein which is aligned with the lateral opening when the slidable cover is in the second position.

10. The refill unit of claim 9, wherein the refill unit is made of plastic.

11. A refill unit according to claim 6, wherein the seal is an elastic rivet on the slidable cover having a first surface which seals with the lateral opening and a second surface providing a gripping area which facilitates sliding the cover from the first position to the second position to uncover the lateral opening and from the second position to the first position to seal the lateral opening.

12. A refill unit according to claim 6, wherein the slidable cover includes a slot therein which is aligned with the lateral opening when the slidable cover is in the second position.

* * * * *